United States Patent
Casavant (10) Patent No.: US 6,330,477 B1
(45) Date of Patent: Dec. 11, 2001

(54) VENTRICULAR SYNCHRONIZED ATRIAL PACING MODE OF IMPLANTABLE CARDIOVERTER/DEFIBRILLATOR

(75) Inventor: David A. Casavant, Reading, MA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/290,519

(22) Filed: Apr. 12, 1999

(51) Int. Cl.[7] ................................................. A61N 1/362
(52) U.S. Cl. .................................................. 607/14
(58) Field of Search ............................ 607/4, 14, 5

(56) References Cited

U.S. PATENT DOCUMENTS

| | | |
|---|---|---|
| 4,284,082 | 8/1981 | Funke et al. . |
| 4,398,536 | 8/1983 | Nappholz et al. . |
| 4,427,011 | 1/1984 | Spurrell et al. . |
| 4,503,857 | 3/1985 | Boute et al. . |
| 4,562,841 | 1/1986 | Brockway et al. . |
| 4,587,970 | 5/1986 | Holley et al. . |
| 4,726,380 | 2/1988 | Vollmann et al. . |
| 4,727,877 | 3/1988 | Kallok . |
| 4,830,006 | 5/1989 | Haluska et al. . |
| 5,074,301 | 12/1991 | Gill . |
| 5,103,822 | 4/1992 | Duncan . |
| 5,163,427 | 11/1992 | Keimel . |
| 5,188,105 | 2/1993 | Keimel . |
| 5,342,402 | 8/1994 | Olson et al. . |
| 5,545,186 | 8/1996 | Olson et al. . |
| 5,713,924 | 2/1998 | Min et al. . |
| 5,735,876 * | 4/1998 | Kroll et al. ............................ 607/5 |
| 5,782,876 | 7/1998 | Flammang . |
| 5,814,079 | 9/1998 | Kieval . |

FOREIGN PATENT DOCUMENTS 9218198    10/1992  (WO) .

OTHER PUBLICATIONS

"Sinus Node Behavior During Stable and Unstable Ventricular Tachycardia with Ventricular–Atrial Dissociation" (*JACC Abstracts*, Feb., 1999, 1204–185).

"Hemodynamic Benefits of Synchronized 1:1 Atrial Pacing During Sustained Ventricular Tachycardia With Severely Depressed Ventricular Function in Coronary Heart Disease" (*Am. J. Cardiol.*, 1985, vol. 55, No. 8, 990–994).

Jutzy, R. V. et al., entitled "Comparative evaluation of rate modulated dual chamber and VVIR Pacing" (PACE, 1990, vol. 12, Part 2. pp. 1838–1846).

* cited by examiner

*Primary Examiner*—William E. Kamm
(74) *Attorney, Agent, or Firm*—Girma Wolde-Michael (57) ABSTRACT

A method and apparatus for alleviating or preventing hemodynamic collapse by delivering ventricular synchronized atrial pacing under certain conditions precedent to or during delivery of an anti-tachyarrhythmia therapy by an implantable cardioverter/defibrillator (ICD) are disclosed. The atrial pacing mode is preferably the AVT pacing mode, wherein the atria (A) are paced, the ventricles (V) are sensed, and the atrial pacing is triggered (T) by the ventricular sense signals. Alternatively, the ADD pacing mode can be employed if the underlying sinus atrial depolarizations can be sensed occasionally as non-refractory, atrial sense signals and employed to inhibit the delivery of an atrial pace pulse. The VS–AP delay between a ventricular sense (VS) and the delivered atrial pace (AP) pulse synchronization of the atrial pacing pulses can be selected to be a function of the prevailing V-V interval of the VT episode. The prevention or alleviation is accomplished by delivering atrial pacing pulses to the atria in synchronization with detected ventricular sense signals, whereby the atrial depolarization rate is increased and synchronized to the ventricular depolarization rate sufficiently to eject blood from the atria into the ventricles to be ejected therefrom upon a subsequent ventricular contraction.

23 Claims, 5 Drawing Sheets

VENTRICULAR SYNCHRONIZED ATRIAL PACING MODE OF IMPLANTABLE CARDIOVERTER/DEFIBRILLATOR

FIELD OF THE INVENTION

The present invention generally relates to implantable medical devices (IMDs), particularly implantable cardioverter/defibrillators (ICDS) for detecting and treating tachyarrhythmias, and more particularly to a method and apparatus for alleviating or preventing hemodynamic collapse under certain conditions precedent to or during delivery of an anti-tachyarrhythmia therapy by the ICD.

BACKGROUND OF THE INVENTION

By way of definition, the term "tachyarrhythmia" refers to any fast, abnormal rhythm of a heart chamber which may be amenable of conversion to a normal sinus rhythm by "cardioversion" or "defibrillation" or the application of certain anti-tachycardia pacing therapies to the heart chamber. Such tachyarrhythmias include ventricular tachycardia (VT), supraventricular tachycardia (SVT), ventricular flutter or fibrillation (VF), atrial tachycardia (AT), and atrial flutter or fibrillation (AF).

In the field of automatic implantable arrhythmia control devices, particularly ICDs (also referred to as pacemaker/cardioverter/defibrillators or PCDs), the terms "cardioversion" or "cardioverter" and "defibrillation" and "defibrillator" generally refer to the processes of and devices for discharging relatively high energy electrical shocks into or across cardiac tissue to arrest a life threatening tachyarrhythmia. In practice, the conversion of AT or VT or low rate AF or VF to normal sinus rhythm by a relatively low amplitude cardioversion shock delivered in timed synchrony with a sensed atrial or ventricular cardiac depolarization (P-wave or R-wave) is typically referred to as "cardioversion". The conversion of malignant AF or VF by the same or higher energy shock delivered without such synchronization is typically referred to as "defibrillation".

Implantable cardiac pacing functions are also currently incorporated into ICDs to supplant some or all of an abnormal heart's natural pacing function by delivering appropriately timed electrical pacing pulses to cause the chamber or chambers of the heart to contract or "beat", i.e., to "capture" the heart. Either single chamber (atrial or ventricular) pacing functions or dual chamber (atrial and ventricular) pacing pulses are applied to the atria and/or the ventricles in response to a detected bradycardia or dissociation of the atrial and ventricular heart rates at a pacing rate to restore cardiac output that is appropriate to the physiologic requirements of the patient. Moreover, anti-tachycardia bursts of pacing pulses or single overdrive pacing pulses are applied to the atria and/or the ventricles to counter and convert certain low rate AT or VT episodes to normal sinus rates. Such pacing pulses have well-defined amplitude and pulse width characteristics which can be adjusted by remote programming and telemetry equipment to meet physiologic needs of the particular patient and device power conservation requirements.

It is known in the ICD art to provide a "tiered" therapy with regard to the termination of sensed tachyarrhythmias. The term "tiered" therapy has been used typically to describe the different tachyarrhythmia rate zones, such as low rate ventricular tachycardia (VT Low), high rate tachycardia (VT High), and VF. The term "tiered therapy" also has been used to describe the increasing degree of aggressiveness within each rate zone. For example, within each zone the physician may program the number and types of therapies to be delivered, the intervals between applied therapies, the energy level of the therapy, etc. Thus, based upon the detected rate of the arrhythmia, the ICD will continue to increase the level of aggressiveness until such arrhythmia is terminated.

Cardioversion is often thought of as being "low energy" since the heart has been known to successfully convert the arrhythmia with electrical shocks in the range of 0.1 to 10 joules. However, it is still classified as cardioversion if the arrhythmia is a ventricular tachycardia even if the energy required to convert the arrhythmia goes up to the maximum value that the ICD is capable of delivering. (e.g., 40 joules). Defibrillation, on the other hand, is often thought of as being "high energy" since the heart has been successfully defibrillated with energy shocks in the range of 11 to 40 joules. In contrast, the pacing pulses that are applied to a heart during normal or anti-tachycardia pacing are typically of much lower energy (e.g., between 50 and 200 micro joules). The principal difference between the types of therapy provided by an ICD supporting tiered therapy is that of arrhythmia detection and the programmed level of aggressiveness with the therapy typically starting by applying the lowest energy stimulation for that detected arrhythmia and working its way up to high energy shock therapy, as required.

To detect and classify tachyarrhythmias, one or two basic strategies are generally followed which start with identifying atrial and/or ventricular sensed events and deriving atrial and/or ventricular event intervals and/or rates therefrom. The event intervals are compared to programmed fibrillation detection interval ranges and tachycardia detection interval ranges and to suddenness of onset criteria and rate variability criteria to distinguish various tachyarrhythmias from one another. In the first strategy, the event intervals are compared with a preset group of criteria which must be met as precedent to detection or classification. As the episode progresses, the first set of criteria to be met results in detection and diagnosis of the tachyarrhythmia. The second strategy is to define a set of criteria for events, event intervals and/or rates which is generally indicative of a group of arrhythmias; following the satisfaction of those criteria, preceding or subsequent events are analyzed to determine which specific tachyarrhythmia is present. The Model 7219 ICD commercially available from Medtronic, Inc., employ an arrhythmia detection and classification system, generally as disclosed in commonly assigned U.S. Pat. No. 5,342,402, incorporated herein by reference in its entirety, which uses both strategies together. Numerous other or additional detection and classification systems have been proposed as set forth in commonly assigned U.S. Pat. Nos. 5,545,186, 5,782,876, and 5,814,079, incorporated herein by reference in their entireties.

Menus of such tachyarrhythmia detection criteria and anti-tachyarrhythmia therapies that are tailored to a range of detected tachyarrhythmias are typically provided in such current ICDs. The above-incorporated patents and U.S. Pat. Nos. 4,830,006, 4,726,380, and 4,587,970, all incorporated herein by reference in their entireties, illustrate such detection criteria and therapy menus. The particular therapies that are to be provided upon detection of particular tachyarrhythmias in an individual patient are remotely programmed into ICD memory by the physician. For example, upon sensing a low rate AT or VT, an ICD may attempt to terminate such a tachycardia by first applying a prescribed anti-tachycardia pacing therapy to the atria or ventricles, respectively. Such anti-tachycardia pacing therapies typically includes burst pacing, ramp pacing, adaptive pacing and/or scanning pacing, as is known in the art. See, e.g., U.S. Pat. Nos. 4,427,011 and 4,541,430 (burst pacing); 4,398,536 (ramp pacing); and 5,103,822 (scanning pacing); which patents are incorporated herein by reference in their entireties. Upon re-detection of the AT or VT, a more aggressive anti-tachycardia pacing therapy may be scheduled.

If the anti-tachycardia pacing therapy is unsuccessful or inappropriate, the ICD may be programmed to apply a low energy, cardioversion energy shock in an attempt to cardiovert the heart. In order to apply a cardioversion or defibrillation shock to a heart chamber, it is first necessary to charge one or more high voltage (HV) output capacitors of the ICD device with to a voltage providing the programmed energy upon discharge through the cardioversion/defibrillation electrodes. When the HV output capacitors are charged to the programmed voltage, HV output switches are closed to connect the HV output capacitor(s) to the cardioversion/defibrillation electrodes, thereby effectively "dumping" the charge stored in the HV output capacitor(s) across the heart chamber.

The tiered therapy ICDs begin to charge their HV output capacitor(s) following initial detection of a tachyarrhythmia or re-detection of the tachyarrhythmia episode that has not been terminated by a previously delivered less aggressive therapy. For example, if the ICD sensing and logic circuits determine that the first tier cardioversion/defibrillation therapy has not successfully terminated the tachyarrhythmia, the HV output capacitors are charged to the appropriate energy for a second tier cardioversion/defibrillation therapy at a higher energy level. As soon as the ICD sensing and logic circuits determine that the second tier cardioversion/defibrillation therapy has not successfully terminated the tachyarrhythmia, the HV output capacitors are charged to a still higher energy level. Unfortunately, it may take 3–4 seconds to charge the high voltage output capacitors to a moderate energy level to (1 to 10 joules), and 7–15 seconds to charge such capacitors to a high energy level (11 to 40 joules). Disadvantageously, these charging times represent a significant period of time, or "time-to-therapy," during which the tachyarrhythmia continues without the benefit of having the ICD apply any therapy.

Considerable effort has been expended in devising efficacious cardiac stimulation and/or shock waveforms and cardioversion/defibrillation electrodes and pathways through the heart in the effort to achieve cardioversion or defibrillation at low energy levels and with shorter charging times. This has been particularly of interest for treating frequently recurring tachyarrhythmias, since the battery life of the ICD depends on the amount of energy expended in delivering a therapy and the delivery frequency.

As noted above, numerous first tier anti-tachycardia pacing therapies have been developed to respond to a given high rate AT or VT preceding delivery of a cardioversion shock in the hope that the low energy pacing pulses would terminate the tachycardia without having to resort to higher energy cardioversion therapies. Or, the low energy pacing pulses have been applied to the heart chamber in the attempt to pre-condition the heart mass to be cardioverted or defibrillated at a lower shock energy. For example, commonly assigned U.S. Pat. No. 5,713,924, incorporated herein by reference discloses delivery of a burst of pacing pulses into a low current density region of the heart chamber prior to and during delivery of a cardioversion/defibrillation shock to that chamber. And, the above-incorporated '079 patent discloses sub-threshold anodal stimulation pulse trains triggered in timed synchronization with a sensed event to a wide area of a heart chamber that is beating at a tachycardia rate to effect maximal cardiac relaxation and to suppress aberrant electrical activity attendant to the sensed cardiac depolarization.

Also, it is known to deliver a pacing pulse following charge up of the HV output capacitors to the heart chamber in the attempt to capture the heart chamber or to make its depolarization more regular to provide the synchronization window for delivery of the cardioversion shock during a refractory period following the delivered pacing pulse. In a further U.S. Pat. No. 5,074,301, a ventricular tachyarrhythmia detection and cardioversion system is disclosed wherein it is proposed to deliver a pacing pulse to the atrium prior to delivery of a cardioversion shock to the ventricle in VT to reduce the possibility that the delivered cardioversion shock would trigger a post-shock atrial arrhythmia. The atrial pacing pulse captures the atrium and renders it refractory, and the ventricular cardioversion shock is delivered during the atrial refractory period.

Hemodynamic collapse is a common condition that occurs during ventricular tachyarrhythmia, particularly in patients having depressed ventricular function. It's severity depends on the rate of the tachyarrhythmia as well as on the responsiveness of the patient's neurally mediated compensatory mechanisms. With drop in blood pressure, arterial baroreceptors invoke a sympathetic vasoconstrictor response to increase peripheral resistance and maintain pressure. Previous work reported by Hamer et al., entitled "Hemodynamic Benefits of Synchronized 1:1 Atrial Pacing During Sustained Ventricular Tachycardia With Severely Depressed Ventricular Function in Coronary Heart Disease" *(Am. J. Cardiol.,* 1985, vol. 55, no. 8,990–94), suggests that this neural reflex may be offset by an opposing reflex involving pressure (or stretch) receptors in the atria. Atrioventricular dyschrony during VT can result in coincident atrial and ventricular contractions which not only results in reversal of blood flow into the veins entering the heart, but also may result in atrial stretch and activation of a vasodilating reflex.

A recent abstract by Wong et al., entitled "Sinus Node Behavior During Stable and Unstable Ventricular Tachycardia with Ventricular-Atrial Dissociation" *(JACC Abstracts,* February 1999, 1204–185), demonstrates the importance of neural reflexes in mitigating hemodynamic collapse during VT. Wong et al. observed that stable VT was characterized by sinus node acceleration whereas unstable VT was not. This work suggests that autonomic modulation of blood pressure does play a role in maintaining blood pressure during VT.

Hemodynamic collapse during unstable ventricular tachyarrhythmias can occur during the initial and succeeding HV charging times if successive, same or tiered therapies are necessary as described above. Although ICDs have been shown to be highly effective in aborting sudden death from malignant ventricular tachyarrhythmias, their ability to prevent syncope or incapacitating pre-syncopal prodromes are limited. This is particularly the case due to the above-described charging time that it takes to charge the HV output capacitors to the prescribed voltage to deliver a cardioversion shock therapy. As a result, ICD patients are advised to significantly curtail or refrain completely from activities that put themselves or others at risk, such as driving a vehicle, operating other equipment, swimming in open water, riding a bicycle, or others that cannot accommodate near or complete loss of consciousness for only a few seconds. For many patients, necessary sacrifices for the sake of safety not only take away their ability to continue to be productive in their professional and in their private lives, but they also restrict their ability to participate in many of life's simple pleasures.

A need exists to avoid or alleviate such hemodynamic collapse following the onset of an unstable VT episode and until an anti-tachycardia cardioversion/defibrillation shock is delivered that successfully converts the ventricles back to normal sinus rhythm.

SUMMARY OF THE INVENTION

Accordingly, the present invention provides a method and apparatus, preferably implemented in an implantable medical device for alleviating or preventing hemodynamic collapse during the operations of an IMD when providing anti-tachyarrhythmia therapies to treat a detected ventricular tachyarrhythmia. The method and apparatus is intended to prevent or alleviate hemodynamic collapse of a patient suffering cardiac insufficiency due to the ventricular tachyarrhythmia pending delivery of an initial ventricular anti-tachyarrhythmia therapy and/or subsequent ventricular anti-tachyarrhythmia therapies delivered in a sequence of therapies. The prevention or alleviation is accomplished by delivering synchronized atrial pacing pulses to prevent hemodynamic collapse pending the delivery of the anti-tachyarrhythmia therapy. The atrial pacing rate may be any rate exceeding the intrinsic atrial rate that suffices to alleviate or prevent the hemodynamic collapse but not at such a high rate that could initiate an atrial tachyarrhythmia.

The particular detected ventricular tachyarrhythmia of greatest interest is an unstable VT episode that exhibits ventricular sense signals, e.g., R-waves, that can be sensed and employed in VT detection and leads to hemodynamic collapse if untreated. In accordance with the present invention, a detected VT episode in a prescribed ventricular rate zone is presumed to be unstable. In this case, prevention or alleviation of hemodynamic collapse is accomplished by delivering atrial pacing pulses to the atria in synchronization with detected ventricular sense signals whenever possible.

The atrial pacing mode is preferably the AVT pacing mode, wherein the atria (A) are paced, the ventricles (V) are sensed, and the atrial pacing is triggered (T) by the ventricular sense signals. Alternatively, the ADD pacing mode can be employed to avoid competitive pacing with underlying sinus originating or retrogradely conducted atrial depolarizations. The use of the ADD pacing mode thereby allows atrial events to be sensed as non-refractory, atrial sensed signals and employed to inhibit the delivery of an atrial pace pulse. The VS–AP delay between a ventricular sense (VS) and the delivered atrial pace (AP) pulse can be selected to be a function of the prevailing V-V interval of the VT episode.

The implantable medical device generates and delivers an antitachycardia therapy to the ventricles of the heart following detection of the VT and in conjunction with the delivery of the ventricular synchronized, atrial pacing pulses in the AVT or ADD pacing mode. The ventricular synchronized, atrial pacing pulses are preferably delivered during application of an anti-tachycardia therapy which may either consist of anti-tachycardia pacing (ATP) or cardioversion (CV) therapy.

The ventricular synchronized, atrial pacing pulses are preferably delivered during ATP therapy delivery in a modified AVT (or ADD) mode whereby ventricular paced (or sensed) events trigger atrial pacing at a prescribed VS–AP delay. During charging precedent to delivery of any CV therapy, ventricular synchronized atrial pacing is delivered in an AVT mode whereby ventricular sensed events detected within the VT zone trigger atrial pacing following the VS–AP delay.

In this way, the patient suffering from a hemodynamically unstable VT may be maintained for a longer period of time with adequate cardiac output to avoid loss of consciousness pending delivery of anti-tachycardia therapies. The patient may have more conscious time to respond to a warning that the VT has been detected and a therapy is to be delivered. While the invention has particular applicability in response to hemodynamically unstable VTs, it is not necessary to determine a priori that the patient will suffer hemodynamic collapse due to a given tachyarrhythmia. The invention can be invoked and employed following detection of any VT and may be beneficially used in conjunction with the detection of other tachyarrhythmias and delivery of other anti-tachyarrhythmia therapies.

This summary of the invention and the advantages and features thereof have been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

Other advantages and features of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

The preferred embodiments of the invention are preferably implemented in the context of an implantable, dual chamber, ICD at least having ventricular anti-tachyarrhythmia capabilities and dual chamber pacing capabilities of the type described in detail in the above-incorporated '186 patent, for example. Such ICDs may be constructed or made programmable to provide atrial only, ventricular only, or both atrial and ventricular pacing modes during bradycardia episodes and the atrial pacing function of the present invention at the prescribed times during certain regular interval ventricular tachycardias. In addition, the present invention may be employed with a wide variety of pacing and cardioversion/defibrillation electrode combinations.

Figure 1:
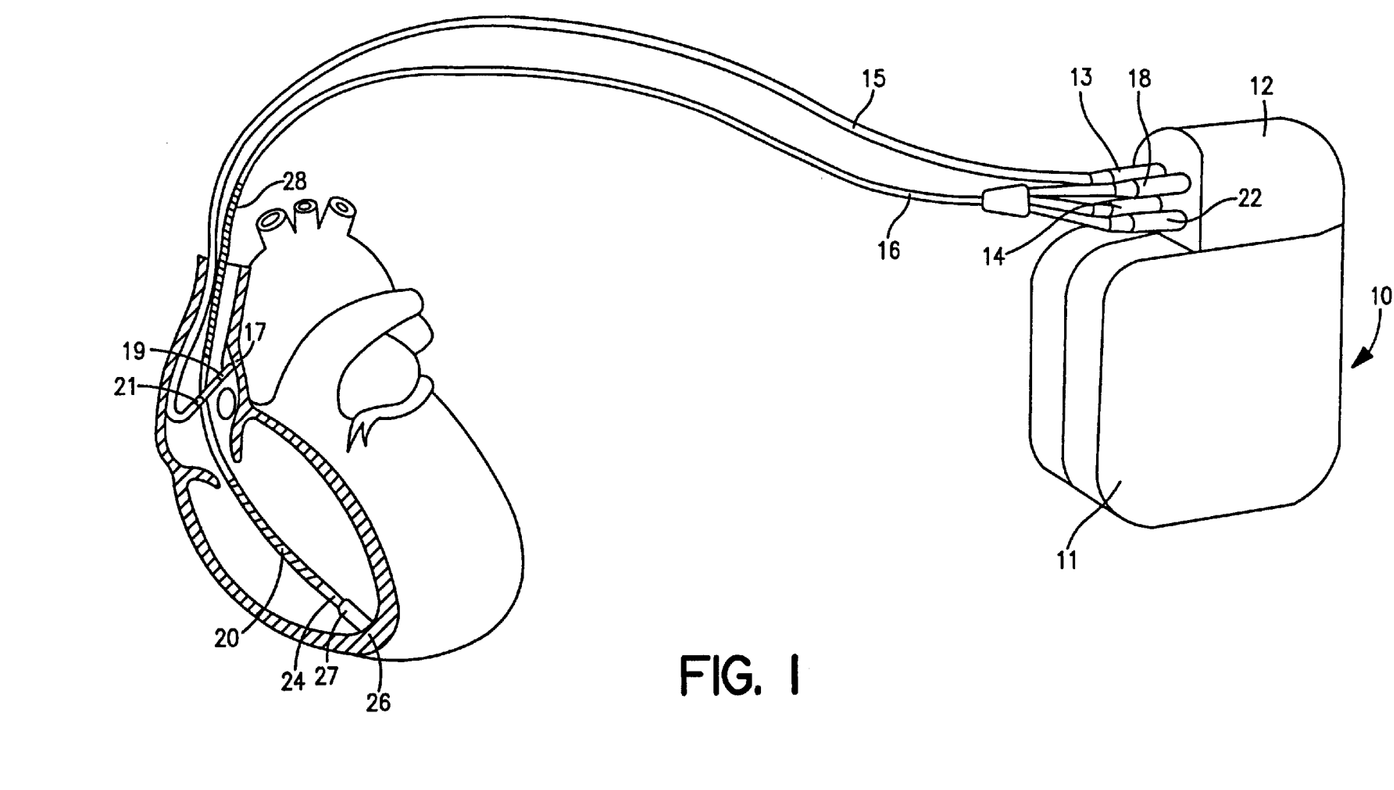
FIG. 1 is a schematic illustration of an atrial and ventricular ICD IPG adapted to be implanted in a patient's chest with an IPG can electrode and endocardial leads transvenously introduced into the heart chambers wherein atrial pacing pulses are delivered during an unstable VT episode precedent to the delivery of an anti-tachycardia therapy to enhance hemodynamic function; in accordance with the invention.
Figure 2:
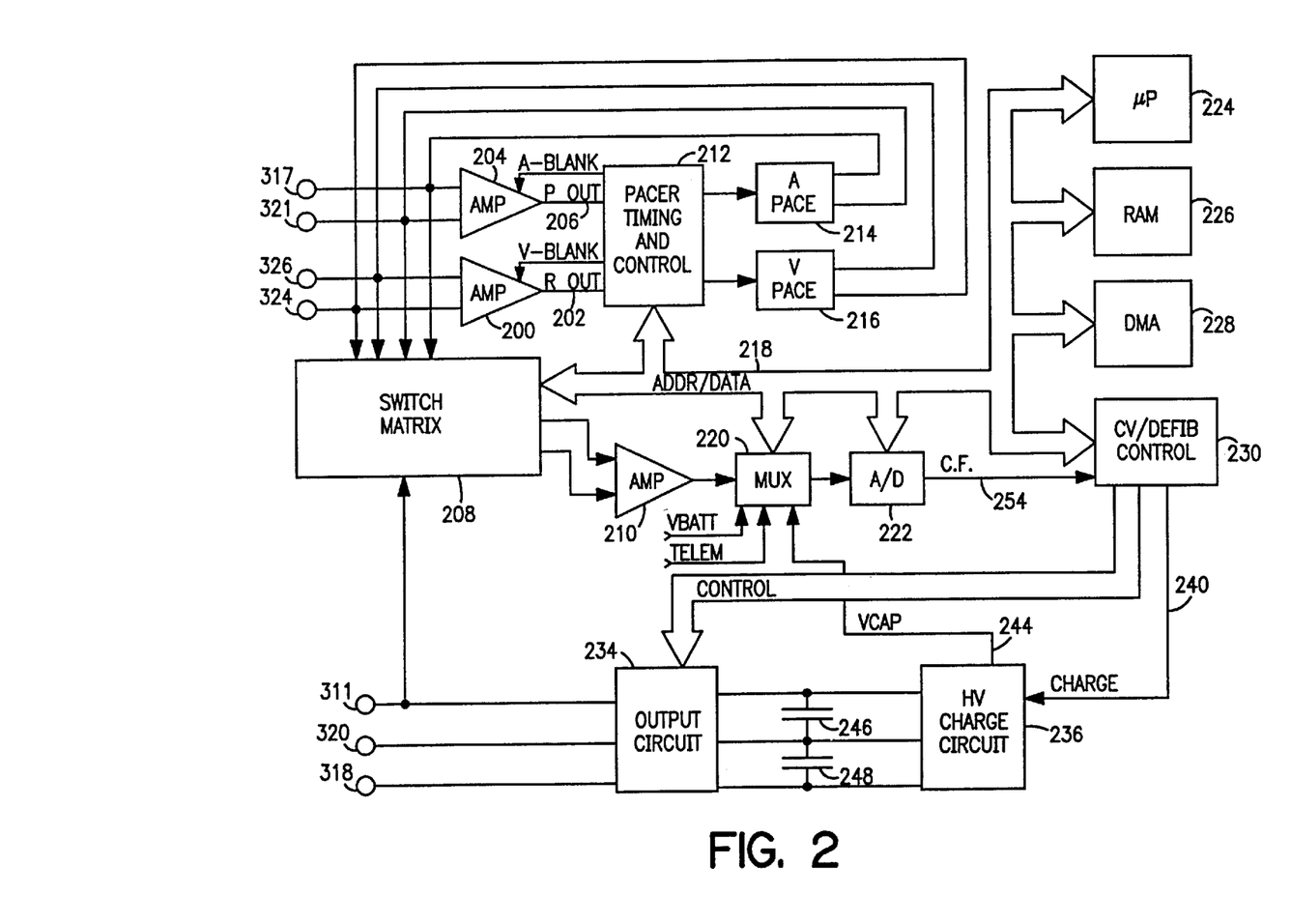
FIG. 2 is a block diagram of an exemplary ICD IPG operating system in which the present invention may be practiced.

FIGS. 1 and 2 illustrate such a dual chamber, multi-programmable, ICD IPG and associated lead system for providing atrial and/or ventricular sensing functions for detecting P-waves of atrial depolarizations and/or R-waves of ventricular depolarizations, depending on the programmed pacing and/or sensing mode and delivering pacing or cardioversion/defibrillation therapies. An exemplary defibrillation lead system is depicted in FIG. 1 for delivering cardioversion/defibrillation shock therapies to the atria or ventricles of the heart. FIGS. 1 and 2 are intended to provide a comprehensive illustration of each of the atrial and/or ventricular, pacing and/or cardioversion/defibrillation configurations that may be effected using sub-combinations of the components depicted therein and equivalents thereto. Preferably, bipolar pace/sense electrodes are employed in the practice of the invention, but their configuration, fixation in contact with, and positioning with respect to the atria and ventricles may differ from those shown in FIG. 1. Unipolar pace/sense electrode bearing leads may also be used in the practice of the invention, and the second, return electrode may be one or more of the defibrillation electrodes.

FIG. 1 illustrates an ICD IPG 10 and a lead set comprising leads 15 and 16 extending to the atrial and ventricular chambers of heart 30 that can be employed in the practice of the present invention. The ICD IPG is formed of a hermetically sealed housing 11 enclosing the electronic circuitry and battery of the ICD system and a connector block 12 containing electrical connectors for coupling the various connector rings and pins of the proximal lead connectors 13, 14, 18 and 22 of the leads 15 and 16. Optionally, insulation of the outward facing portion of the housing 11 of the ICD IPG 10 may be provided in the form of a plastic coating, for example parylene or silicone rubber, as is currently employed in some unipolar cardiac pacemakers. However, the outward facing portion may instead be left un-insulated, or some other division between insulated and un-insulated portions may be employed. The un-insulated portion of the housing 11 can then serve as a subcutaneous cardioversion/defibrillation electrode.

The ventricular lead 16 includes an elongated, non-conductive, bio-compatible lead body enclosing four mutually insulated lead conductors. A ring shaped pace/sense electrode 24, an extendable helix pace/sense electrode 26, mounted retractably within an non-conductive electrode head 27, and two elongated coil cardioversion/defibrillation electrodes 20 and 28 are located on lead body 16 and coupled to distal ends of one of the coiled conductors within the lead body 16. Ventricular pace/sense electrodes 24 and 26 are employed for applying cardiac pacing pulses to the ventricle and for sensing ventricular depolarizations or R-waves. Cardioversion/defibrillation electrodes 20 and 28 are employed in conjunction with the conductive housing 11 of the ICD IPG 10 for delivery of ventricular cardioversion and defibrillation pulses. Ventricular lead 16 is formed with three bifurcated proximal connectors 14, 18 and 22 coupled with the proximal ends of the lead conductors within the lead body. Unipolar connectors 18 and 22 each terminate in connector pins coupled to the proximal ends of the lead conductors coupled with the coiled cardioversion/defibrillation electrodes 20 and 28, respectively. Proximal connector 14 is an in-line bipolar connector carrying a connector ring and a connector pin that are coupled through lead conductors to ventricular pace/sense electrodes 24 and 26, respectively.

The conventional bipolar atrial pacing lead 15 includes an elongated non-conductive lead body enclosing two concentric coiled wire lead conductors that are separated from one another by tubular non-conductive sheaths and extend from the proximal connector 13 to atrial pace/sense electrodes 21 and 17 disposed in the right atrium. The ring-shaped atrial pace/sense electrode 21 and an extendable helix, atrial pace/sense electrode 17, mounted retractably within an non-conductive electrode head 19, are located adjacent the J-shaped distal end of the atrial pacing lead body and are employed for atrial pacing and for sensing atrial depolarizations or P-waves. In alternative atrial lead systems, a cardioversion/defibrillation electrode, for example corresponding to cardioversion/defibrillation electrode 28, might instead be mounted to the atrial lead 15 as shown in FIG. 1 of the above-incorporated '924 patent, for example. A further coronary sinus cardioversion/defibrillation lead could also be employed in the ICD system for location in the coronary sinus and great cardiac vein as also shown in FIG. 1 of the above-incorporated '924 patent, for example.

FIG. 2 is a functional schematic diagram of an ICD IPG operating system 100 which may be enclosed within the IPG housing 11 and with which the present invention may usefully be practiced. This diagram should be taken as exemplary of the type of ICD system in which the invention may be embodied, and not as limiting, as it is believed that the invention may usefully be practiced in a wide variety of device implementations. Such implementations include ICD systems providing therapies for treating atrial tachyarrhythmias in addition to ventricular tachyarrhythmias and ICDs which do not provide anti-tachycardia pacing therapies.

The ICD IPG operating system 100 includes a HV section for providing relatively HV cardioversion/defibrillation shocks when needed in response to detection of a tachyarrhythmia and a low voltage pace/sense section for sensing P-waves and/or R-waves and providing relatively low voltage bradycardia pacing and anti-tachycardia pacing therapies. Other functions, including uplink and downlink telemetry with an external programmer for interrogating or programming operating modes and parameters, are also provided in a manner well known in the art.

The operations of ICD system 100 are controlled by a microcomputer comprising the microprocessor 224 operating using stored programs and operating mode and parameter value data stored in RAM/ROM unit 226 and pacer timing/control circuitry 212. Microprocessor 224 operates as an interrupt driven device, and is responsive to interrupts from pacer timing/control circuitry 212 corresponding to the occurrences of sensed P-waves and R-waves and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts. A portion of the RAM in RAM/ROM unit 226 may be configured as a plurality of recirculating buffers, capable of holding series of measured intervals, which may be analyzed in response to the occurrence of a pace or sense interrupt to determine whether the patient's heart is presently exhibiting atrial or ventricular bradycardia or normal sinus rhythm or tachyarrhythmia.

The ICD system 100 includes a set of cardioversion/defibrillation terminals 311, 318 and 320 and a set of pace/sense terminals 317, 321, 326 and 324 that are coupled via housing feedthroughs (not shown) to connector elements of the header 12 of the ICD IPG 10 of FIG. 1. Cardioversion/defibrillation terminals 311, 318 and 320 are coupled to high voltage output circuit 234. Terminal 311 is coupled to a cardioversion/defibrillation electrode that is formed of the uninsulated portion of the housing 11 of the ICD IPG 10. Terminal 320 is coupled to cardioversion/defibrillation electrode 20 located in the right ventricle. Terminal 318 is coupled to cardioversion/defibrillation electrode 28 located in the superior vena cava.

Ventricular pace/sense terminals 324 and 326 are coupled to ventricular pace/sense electrodes 24 and 26 through lead 16 as described above. Ventricular pace/sense terminals 324 and 326 are also coupled to the input terminals of R-wave sense amplifier 200 and to the output terminals of the V-Pace output circuit 216. R-wave sense amplifier 200 preferably takes the form of an automatic gain controlled amplifier providing an adjustable sensing threshold as a function of the measured R-wave amplitude. A ventricular sense or VSENSE signal is generated on R-out line 202 whenever the signal sensed between terminals 324 and 326 exceeds the ventricular sensing threshold.

Atrial pace/sense terminals 317 and 321 are coupled to atrial pace/sense electrodes 17 and 21 through lead 15 as described above. Atrial pace/sense terminals 317 and 321 are also coupled to the input terminals of P-wave sense amplifier 204 and to the output terminals of the A-Pace output circuit 214. P-wave sense amplifier 204 preferably also takes the form of an automatic gain controlled amplifier providing an adjustable sensing threshold as a function of the measured P-wave amplitude. An atrial sense or ASENSE signal is generated on P-out line 206 whenever the signal sensed between terminals 317 and 321 exceeds the atrial sensing threshold.

The A-Pace output circuit 214 generates an atrial pacing pulse applied to terminals 317 and 321 in response to an atrial pace trigger signal generated by the pacer timing and control circuitry 212. Similarly, the V-Pace output circuit 216 generates a ventricular pacing pulse applied to terminals 324 and 326 in response to an ventricular pace trigger signal generated by the pacer timing and control circuitry 212.

The atrial and ventricular sense amplifiers 204 and 200 are isolated from the A-Pace and V-Pace output circuits 214 and 216 by appropriate isolation switches and also by blanking circuitry operated by A-BLANK and V-BLANK signals during and for a short time following delivery of a pacing pulse in a manner well known in the art. The general operation of the R-wave and P-wave sense amplifiers 200 and 204 may correspond to that disclosed in U.S. Pat. No. 5,117,824, incorporated herein by reference in its entirety.

A switch matrix 208 is used to select which of the available atrial and ventricular pace/sense electrodes and the remote electrode formed on the IPG housing 11 are coupled in far field and near field sensing combinations to wide band (0.5–200 Hz) EGM amplifier 210 for use in EGM signal analysis and storage. Selection of terminal pairs from the available terminals 317, 321, 326, 324 and 311 is controlled by the microprocessor 224 via data/address bus 218, which selections may be programmed by the physician. EGM output signals of bandpass amplifier 210 are provided to multiplexer 220 and are thereafter converted to multi-bit digital signals by A/D converter 222 for storage in RAM in RAM/ROM unit 226, under control of direct memory access (DMA) circuit 228. Microprocessor 224 may employ digital signal and morphology analysis techniques to characterize the digitized signals stored in ROM/RAM 226 to recognize and classify the patient's heart rhythm employing any of the numerous signal processing methodologies known to the art.

The pacer timing/control circuitry 212 includes programmable digital counters which control the basic time intervals associated with DDD, VVI, DVI, VDD, AAI, DDI and other modes of single and dual chamber pacing for treating bradycardia and AV dissociation well known to the art. Circuitry 212 also controls escape intervals associated with anti-tachyarrhythmia pacing in both the atrium and the ventricle, employing any anti-tachyarrhythmia pacing therapies known to the art. Pacer timing and control circuitry 212 controls atrial and/or ventricular pacing in response to a bradycardia or AV dissociation employing programmed parameter values and operating modes stored in RAM in RAM/ROM unit 226 in a manner well known in the art. Pacer timing and control circuitry 212 times out atrial and ventricular escape intervals, AV intervals, ventricular safety pacing intervals, refractory periods during which sensed P-waves and R-waves are ineffective to restart timing of the atrial and ventricular escape intervals and the pulse energy of the pacing pulses. These parameters are determined by microprocessor 224 in response to the stored data in RAM in RAM/ROM unit 226 and are communicated to the pacing circuitry 212 via address/data bus 218.

The atrial and ventricular escape interval and AV delay timers within pacer timing/control circuitry 212 are reset by ASENSE and VSENSE signals on lines 202 and 206 and by generation of atrial and ventricular pacing pulses in accordance with the selected mode of pacing. The escape interval timers can also be employed in anti-tachycardia pacing modes to time out the delivery of anti-tachycardia pacing pulses. The intervals defined by the escape interval timers are determined by microprocessor 224, via data/address bus 218.

Moreover, when the escape interval timers are reset by ASENSE and VSENSE signals, the elapsed time in the timers can be used to detect and classify atrial and ventricular tachyarrhythmia episodes. The arrhythmia detection methods that are employed may include any of the tachyarrhythmia detection algorithms known in the art.

In the event that an atrial or ventricular tachyarrhythmia is detected, and an anti-tachyarrhythmia pacing regimen is programmed, appropriate timing intervals for controlling generation of anti-tachyarrhythmia pacing therapies are loaded from microprocessor 224 into the pacer timing and control circuitry 212. The pacer timing and control circuitry 212 controls the operation of the escape interval timers and times out refractory periods during which detection of R-waves and P-waves is ineffective to restart the escape interval timers. The A-Pace output circuit 214 or the V-Pace output circuit 216 is selectively triggered by an atrial pace trigger signal at the expiration of the atrial or ventricular escape interval timer to deliver the atrial or ventricular pacing pulses to the atrium or ventricle, respectively.

Microprocessor 224 responds to the detection of atrial or ventricular fibrillation or tachyarrhythmia requiring a cardioversion therapy and activates cardioversion/defibrillation control circuitry 230. Cardioversion/defibrillation control circuitry 230 applies a CHARGE signal via HV charging control line 240 to the HV charge control circuit 236 to initiate charging of the HV output capacitors 246, 248. The voltage on the HV output capacitors 246, 248 is monitored via VCAP line 244, which is passed through multiplexer 220. A logic signal on Cap Full (CF) line 254 is generated when the HV capacitor voltage on the VCAP line 244 reaches a predetermined value set by microprocessor 224. The logic signal on Cap Full (CF) line 254 is applied to cardioversion/defibrillation control circuitry 230 which responds by terminating the CHARGE signal.

Thereafter, timing of the delivery of the defibrillation or cardioversion pulse via the terminals 311, 320 and 318 is controlled by pacer timing/control circuitry 212. Following delivery of the fibrillation or tachycardia therapy the microprocessor 224 then returns the operating mode to the cardiac pacing mode and awaits the next successive interrupt due to pacing or the occurrence of a sensed atrial or ventricular depolarization.

One embodiment of an appropriate system for delivery and synchronization of ventricular cardioversion and defibrillation pulses and for controlling the timing functions related to them is disclosed in more detail in commonly assigned U.S. Pat. No. 5,188,105, incorporated herein by reference in its entirety. If atrial cardioversion/defibrillation capabilities are included in the ICD system 100, appropriate systems for delivery and synchronization of atrial cardioversion and defibrillation pulses and for controlling the timing functions related to them may be found in published PCT Patent Application No. WO 92/18198, incorporated herein by reference in its entirety.

In the illustrated ICD system 100, delivery of the cardioversion or defibrillation pulses is accomplished by HV output circuit 234, under control of control circuitry 230 via control bus 238. HV output circuit 234 determines whether a monophasic or biphasic cardioversion/defibrillation shock is delivered, whether the housing electrode serves as cathode or anode and which of the other electrodes 20 and 28 are employed in delivery of the shock. An example of output circuitry for delivery of biphasic pulse regimens may be found in U.S. Pat. No. 4,727,877, incorporated by reference in its entirety. An example of circuitry which may be used to control delivery of monophasic pulses is set forth in commonly assigned U.S. Pat. No. 5,163,427, also incorporated herein by reference in its entirety. As described at the outset, in modern ICD IPGs, the particular therapies are programmed in during a patient work up by the physician, and a menu of therapies is typically provided. The present invention is directed to a programmable therapy enhancement that alleviates hemodynamic collapse following the onset of a VT episode that may constitute a hemodynamically unstable VT episode and until an anti-tachycardia therapy is delivered that successfully converts the ventricles back to normal sinus rhythm. It is believed that the atria can be paced to synchronously contract with high rate contractions of the ventricles during VT episodes that are relatively regular (i.e., do not fluctuate significantly) so that atrial contractions actively fill the ventricles with blood that is then ejected from the ventricles. When the atria fail to contract and relax in synchrony with the ventricles that are rapidly contracting and relaxing due to a VT, coincident atrial and ventricular contraction can occur resulting in backflow of blood into the venous system accompanied by atrial stretch.

Although the contribution of active atrial filling of the ventricles to cardiac output appears to most important at resting heart rates, there does appear to be an incremental benefit at higher rates. A paper by Jutzy, R. V. et al., entitled "Comparative evaluation of rate modulated dual chamber and VVIR Pacing" (PACE, 1990, vol.12, Part 2, pp.1838–1846), comparing DDDR to VVIR pacing validates this assertion. The above-referenced article by Hamer et al. has demonstrated that ventricular triggered atrial pacing during an unstable VT episode may offer hemodynamic benefit and may be especially important in patients with compromised left ventricular function. This scientific evidence supports the proposition of this invention that atrial pacing synchronized to ventricular contractions during certain unstable VT episodes prior to and between successive anti-tachycardia therapies would be beneficial to the patient.

Figure 3:
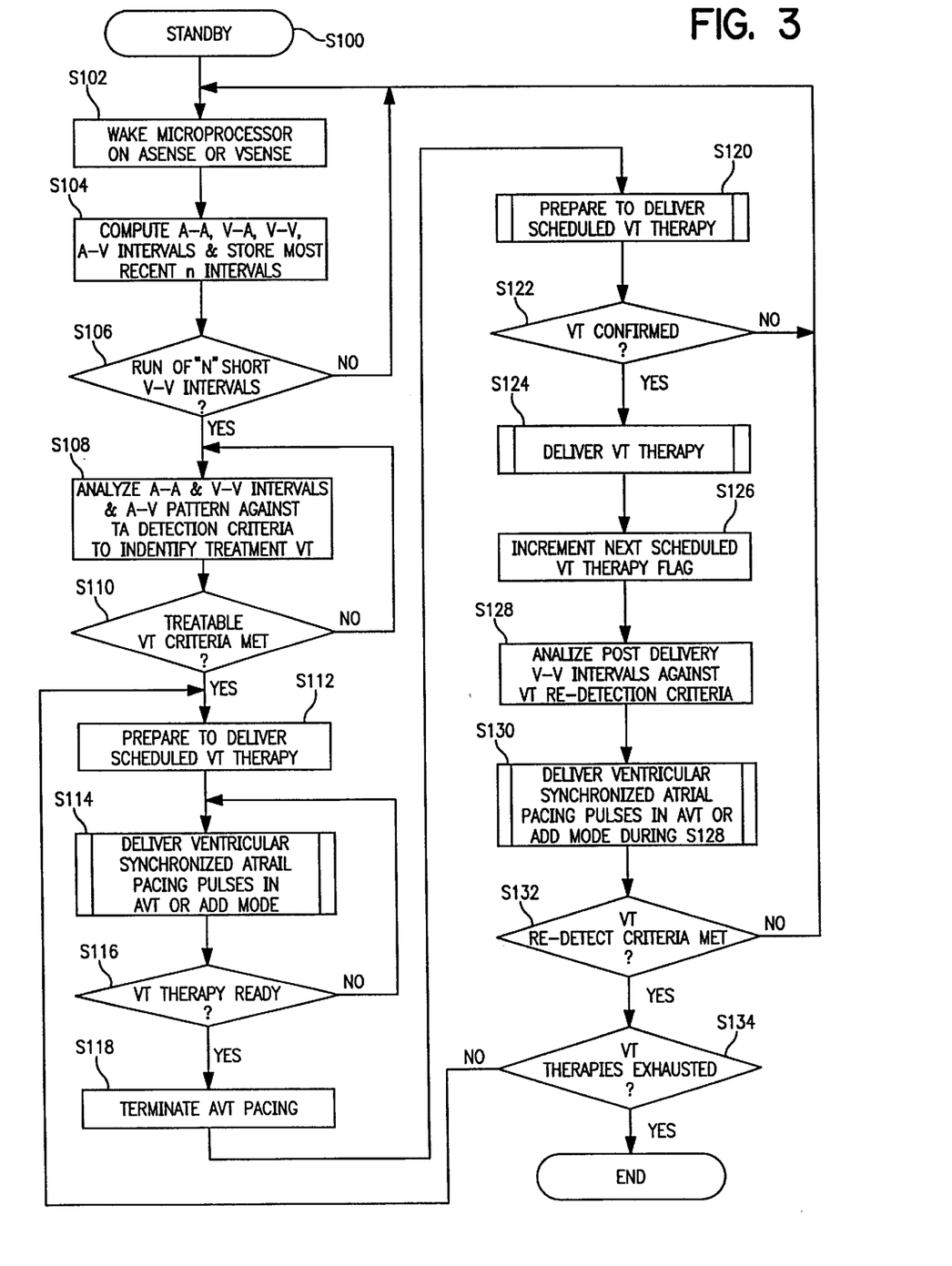
FIG. 3 is a flowchart illustrating the present invention embodied into an ICD system as depicted in FIGS. 1 and 2 wherein atrial pacing pulses are delivered under certain conditions attendant to the delivery of an anti-tachycardia therapy to enhance hemodynamic function.
Figure 4:
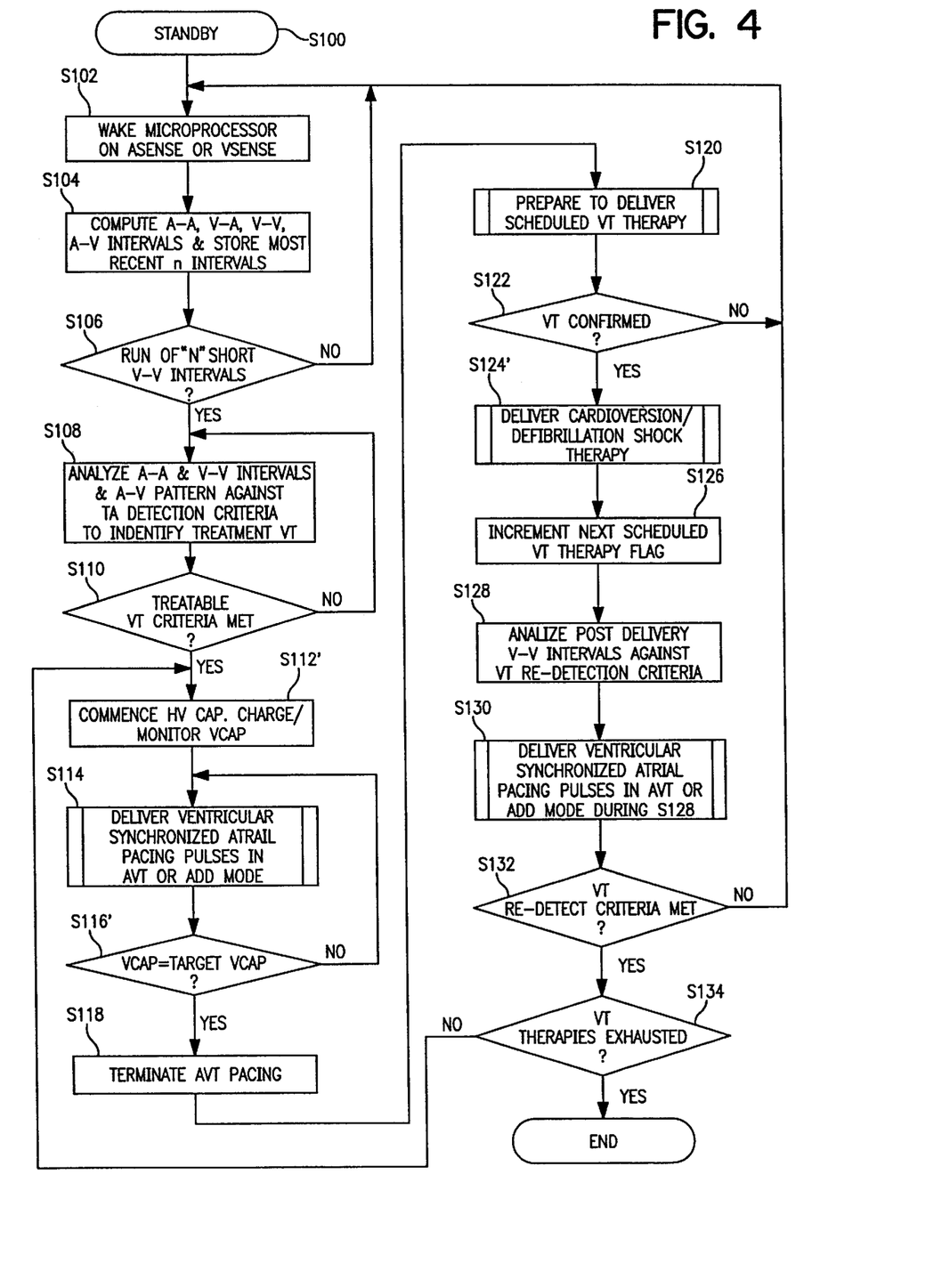
FIG. 4 is a variation of the flowchart of FIG. 3, wherein the anti-tachycardia therapies to be delivered are cardioversion/defibrillation therapies.
Figure 5:
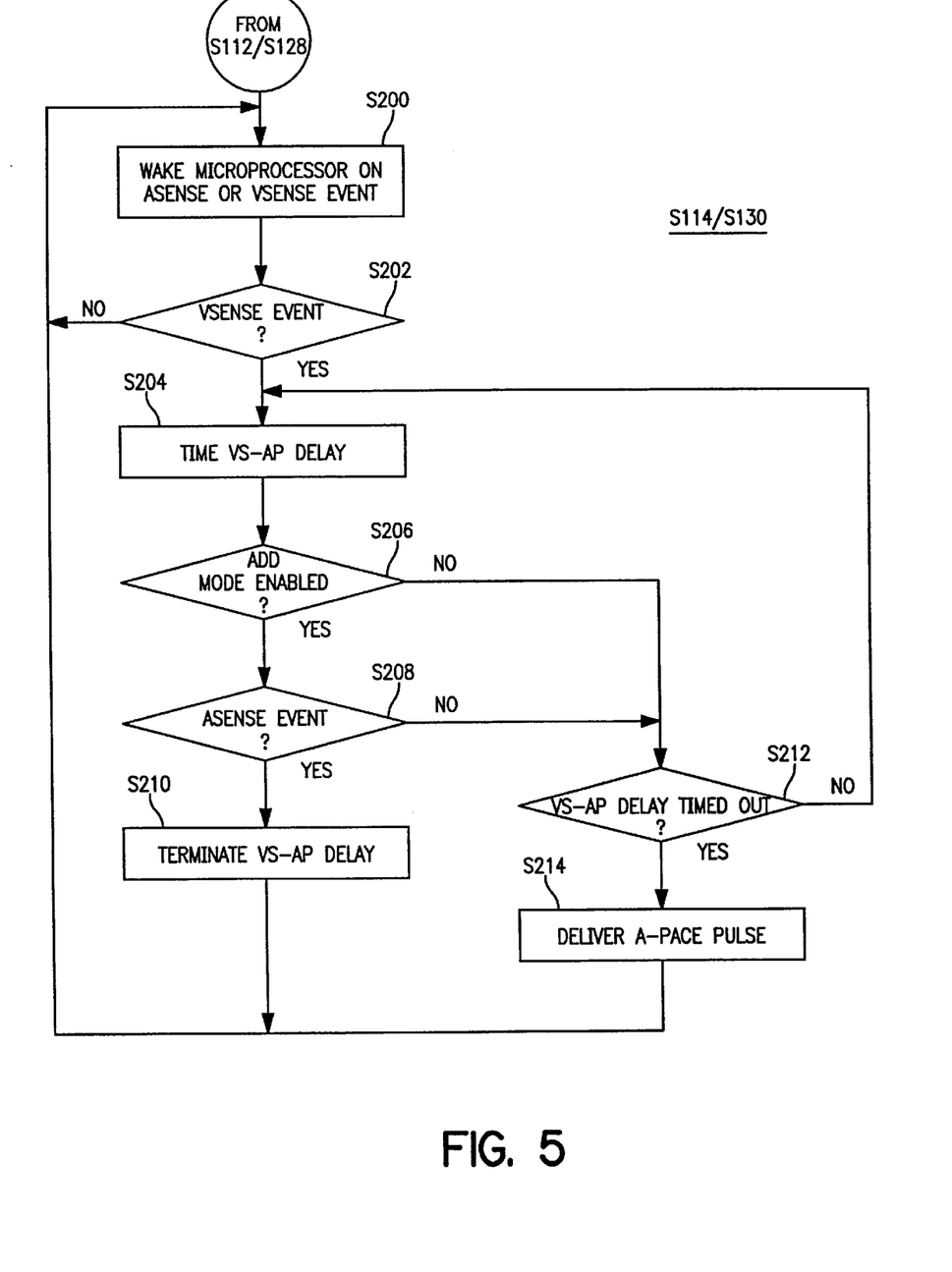
FIG. 5 is a detailed flowchart of steps S114 and S130 of FIGS. 3 and 4.

Accordingly, the present invention is preferably implemented in software or firmware within RAM/ROM unit 226 or hardware circuits incorporated in pacer timing and control circuitry 212 that performs the operations depicted in the flowcharts of FIGS. 3–5.The steps of FIG. 3 illustrate the present invention embodied into an ICD system as depicted in FIGS. 1 and 2 wherein atrial pacing pulses are delivered under certain conditions attendant to the delivery of any anti-tachycardia therapy to enhance hemodynamic function. FIG. 4 is a variation of the flowchart of FIG. 3, wherein the anti-tachycardia therapies to be delivered are cardioversion/defibrillation therapies. Consequently, FIGS. 3 and 4 are described together as follows.

At step S100 of FIGS. 3 and 4, the microprocessor 224 is in the standby mode to conserve battery power. When the patient's heart is beating normally, the ASENSE and VSENSE interrupts (P OUT and R OUT of FIG. 2) are received by the pacer timing and control circuit 212 to reset the various interval timers described above, pacing is inhibited, and none of the anti-tachyarrhythmia therapies are triggered. The microprocessor 224 awakens in step S102 and computes and stores the V-A, and A-A intervals in response to an ASENSE interrupt and computes and stores the V-V and AV intervals in response to the VSENSE interrupts and performs any housekeeping routines. The most recent series of such intervals, extending over the preceding several minutes, and the contemporaneous digitized EGM data are stored in RAM buffers on a FIFO basis. Similar operations take place during atrial or ventricular bradycardia with or without AV dissociation, except that pacing pulses are delivered as described above at a pacing rate that is either programmed or varies in dependence upon a sensed physiologic parameter related to patient activity and/or need to maintain cardiac output.

If a "run of short V-V intervals" indication is provisionally determined as an abnormal cardiac rhythm at step S106, then the main diagnostic routine for determining the type of tachyarrhythmia is commenced in step S108 employing the preceding and subsequently stored interval data and EGM data in the FIFO registers. In the event that a predetermined number of short intervals less than an atrial or ventricular tachycardia detection interval (TDI) or fibrillation detection interval (FDI) occurs during a predetermined time interval or a preceding series of heart cycles, or other threshold criteria, e.g., instability in a series of such intervals, are satisfied in step S106, then the microprocessor 224 commences a routine in step S108 to detect the particular atrial and/or ventricular tachyarrhythmia as described above. The main diagnostic routine of step S108 may employ the rate, onset, and stability criteria and/or other criteria described above and simultaneously compares the accumulated data to a number of possible ventricular tachyarrhythmia models.

In step S110, the main diagnostic routine of step S108 determines if the run of short V-V intervals is regular and constitutes a ventricular tachycardia episode that is to be responded to by delivery of an ATP therapy or a CV shock therapy, or is rapid and irregular and is to be responded to by delivery of an unsynchronized defibrillation (DEFIB) shock therapy. In patients with simultaneous fast atrial rhythms, further analyses of the atrio-ventricular timing patterns is done in step S110 in order to discriminate whether the tachyarrhythmia is supraventricular in origin, which does not respond to ICD therapy, or whether a dual tachyarrhythmia consisting of independently rapid rhythms in both the atria and ventricles (e.g., AF+VT) is present.

A given VT episode may be further characterized as VT or "fast" VT (FVT) in step S110, although it is not determinable with certainty that the VT episode will in each instance result in hemodynamic collapse. In this illustrated embodiment of the present invention, the tachyarrhythmia of interest is a VT (or FVT) satisfying certain rate and regularity criteria such that it is possible to accurately detect R-waves that truly reflect ventricular depolarizations. The tachyarrhythmia of interest is neither supraventricular in origin nor is accompanied by a simultaneous atrial tachyarrhythmia (i.e. dual tachycardia). Certain VT episodes result in regular but less forceful contractions of the ventricles during which atrial pacing pulses can be synchronously timed and delivered to augment ventricular filling and to prevent backflow and atrial stretch that occurs with coincident atrial and ventricular contraction.

The timing relationship of the A-A intervals and the V-V intervals can also be analyzed in step S108 and taken into account in step S110. When the atrial heart rate is monitored along with the ventricular heart rate in a dual chamber ICD system, it is possible to determine from the A-A, A-V, V-, and V-V intervals whether the atria and ventricles are depolarizing in synchrony as a result of ventriculo-atrial (i.e., retrograde) activation during VT.. If the examination of the A-A intervals and the V-V intervals in step S108 cannot positively establish that there is a 1:1 V-A relationship during a VT episode, it will be assumed that the VT episode is treatable by AVT pacing in step S114.

If the determination of an unstable VT is made in step S10, a scheduled VT therapy is called upon which may be an anti-tachycardia pacing therapy in step S112 of FIG. 3 or a cardioversion/defibrillation shock therapy S112' of FIG. 4. If an anti-tachycardia pacing therapy is to be delivered, it will be delivered by the pacer timing and control circuit 212 generating bursts of V-PACE trigger pulses. If a synchronized cardioversion or un-synchronized defibrillation shock therapy is prescribed as shown in step S112' of FIG. 4, then the CV/DEFIB control circuit 230 of FIG. 2 is enabled in step S112' to commence charging the HV output capacitors 246 and 248 through HV charge circuit 244 until they are charged to the programmed voltage at the end of the charging time. After charging to the programmed voltage is completed, the HV switches in the HV output circuit 234 are to be closed to discharge the HV output capacitors 246 and 248 across the selected cardioversion/defibrillation electrodes, either with or without synchronization with a VSENSE signal.

In accordance with the present invention, ventricular synchronized atrial pacing pulses are generated in A-Pace output circuit 214 and delivered via terminals 317 and 321 and lead 15 to the atrial pace/sense electrodes 17 and 21 to pace the atria in an AVT or ADD pacing mode in step S114 during any delay preceding delivery of an anti-tachycardia pacing therapy or that charging time. The atria are thereby paced to contract at the same rate as the ventricles and in timed synchrony with the ventricles in step S114, shown in greater detail in FIG. 5.

The AVT (or ADD) pacing mode is terminated in step S118 when the delay attendant to the delivery of the VT therapy expires as determined in step S116 or the HV output capacitors 246 and 248 are charged over a charging delay to the programmed, target VCAP as determined in step S116'. Thus, high rate atrial pacing in the AVT (or ADD) pacing mode is maintained from the time that the VT episode is detected in step S110 until the VT therapy, e.g., the CV/DEFIB shock, is ready to be delivered with the intention of mitigating hemodynamic collapse in that time period.

In the AVT (or ADD) ventricular synchronized, atrial pacing mode, A-PACE pulses are triggered and generated by A-Pace output circuit 214 after the time-out of a VS-AP (VSENSE signal to A-PACE output) delay set by microprocessor 224 and timed by pacer timing and control circuit 212 of FIG. 2. In the AVT mode, spontaneous ASENSE signals that could occur during the VS-AP delay are ignored, whereas in the ADD mode, non-refractory ASENSE signals occurring near the end of the VS-AP delay inhibit delivery of the A-PACE pulse that would otherwise be triggered.

FIG. 5 is a detailed flowchart of steps S114 and S130 of FIGS. 3 and 4. At step S200, the microprocessor 224 is awakened upon an ASENSE signal or a VSENSE signal. If a VSENSE signal occurs in step S202, then the VS-AP delay is timed in step S204. The VS-AP delay may be a fixed delay or an adaptive delay that is proportional to the V-V interval. In either case, the atria are to be paced between successive VSENSE signals, that is between ventricular contractions to provide an AP-VS (A-PACE to VSENSE) delay that is adequate to provide atrial contraction and ejection of atrial blood into the ventricles while the ventricles are relaxed and before the next ventricular contraction occurs.

The AVT pacing mode is the default mode, and so the ADD pacing mode must be enabled by programming it on, for example. If the ADD mode is enabled as determined in step S206, then a non-refractory ASENSE interrupt to the microprocessor in step S200 are taken into account. The non-refractory ASENSE signal terminates the VS-AP delay in step S210 if the ASENSE signal occurs while the VS-AP delay is being timed out. A refractory period can be timed from the VSENSE signals so that far field VSENSE signals that are sensed by the P-wave sense amplifier 204 are not mistakenly detected as ASENSE signals and inhibit the delivery of the A-PACE pulse.

If the ADD mode is not enabled in step S206, then the VS-AP delay times out in step S212, and the A-Pace pulse is delivered in step S214. The steps S200–S214 of step S116 continue until terminated in step S118 after VT therapy is ready to be delivered as determined in step S116 or the HV output capacitors 118 are charged as determined in step S116'. Steps S102–S110 continue while steps S112–S118 are carried out, and then, in step S120, the earlier VT detection is confirmed in a manner well known in the art. If the VT is not confirmed in step S120, as determined in step S122, then, the VT episode has either spontaneously reverted to normal sinus rhythm or changed to a different tachyarrhythmia as determined in steps S102–S108. In either case, the delivery of the CV/DEFIB shock therapy is aborted.

Upon confirmation in step S122, the VT therapy is delivered In step S124 or the CV/DEFIB shock therapy is delivered in step S124'. As noted above, steps S102 and S104 continue while steps S106–S120 are carried out, but then the R-wave and P-wave sense amplifiers 204 and 200 and the EGM sense amplifier 210 are blanked during delivery of the CV/DEFIB shock in step S124' and for a recovery period thereafter to allow energy to dissipate from the tissue adjacent to the pace/sense electrodes. Then, the R-wave and P-wave sense amplifiers 204 and 200 and the EGM sense amplifier 210 are again enabled to continue with steps S102 and S104. Certain anti-tachycardia burst pacing therapies can be delivered with very short blanking periods following each V-PACE pulse of the burst allowing inhibition upon detection of a VSENSE signal.

The next scheduled VT therapy count or flag is incremented in step S126 to allow identification in step S112 of the next VT therapy to be delivered if the VT episode is not converted in response to the VT therapy delivered in step S124 or 124'.

In step S128, the efficacy of the delivered VT therapy is assessed for a period of time following delivery in step S126 in a manner well known in the art. It may take several seconds to determine if the delivered VT therapy has successfully converted the ventricles to a normal sinus rhythm or if the VT is not successfully converted and is re-detected. The examination of a number of timed V-V intervals, e.g. 12–16 V-V intervals, is conducted in step S128. That examination typically simply involves serially comparing the determined V-V intervals to the VT rate zones, without considering the atrial heart rate or any other stability or onset criteria or the like.

In step S130, the ventricular synchronized atrial pacing in the AVT (or ADD) mode as depicted in FIG. 5 is optionally commenced again at the start of step S128 and continues during the re-detection examination of the set number of V-V intervals. In practice, this feature of step S130 would be programmable ON or OFF by the physician, and the default state of step S130 would be OFF. Step S130 would be programmed ON only for patients that have high degree atrio-ventricular heart block, because ventricular synchronized atrial pacing in the AVT (or ADD) mode in a patient with intact 1:1 A-V conduction could perpetuate a pacemaker mediated ventricular tachycardia that would interfere with redetection. But, in the subset of patients with A-V block, the prolonged duration of ventricular synchronized atrial pacing can be beneficial in reducing hemodynamic collapse.

Steps S112–S124 are then repeated if the VT re-detection criteria are met in step S132 and if the VT therapies are not exhausted as determined in step S134 from the next scheduled VT therapy flag. Typically, if a further VT therapy is to be delivered, a more aggressive therapy, e.g. a higher energy CV/DEFIB shock therapy, is delivered in step S124. The re-detection and delivery of a prescribed VT therapy is repeated until either the re-detection criteria are not satisfied or delivery of all the programmed therapies is completed as determined in step S134.

If the VT is re-detected at step S132 of FIG. 4, and the next CV/DEFIB shock therapy is to be delivered as determined at step S134, the ventricular synchronized atrial pacing is again delivered in the AVT (or ADD) pacing mode in step S116 while the HV output capacitors charge up again. It may take even longer to charge up the HV output capacitors 246 and 248 if a more aggressive, higher energy, CV/DEFIB shock therapy is prescribed.

In this way, synchronized atrial pacing is applied to the atria to alleviate the deterioration in cardiac output and to avoid hemodynamic collapse during that time that the patient may need to halt activities and move to a safe place or position for the CV/DEFIB shock therapy to be delivered. Usually, the patient can feel the onset of ventricular tachyarrhythmia by symptoms of either palpitations or light-headedness due to reduced blood flow to the brain. The maintenance of adequate cardiac output and avoidance of hemodynamic collapse offers the patient additional security and increases patient safety.

The mechanism by which the ventricular synchronized atrial pacing mitigates hemodynamic collapse is believed to be related in part to a degree of active filling of the ventricles that results from restoration of the AV synchrony. In addition, and perhaps more importantly, the contraction and emptying of the atria in response to the atrial pacing pulses suppress a neural reflex that otherwise occurs when the atria are filled with blood and stretched. The atrial walls stretch because of the low sinus atrial rate of contraction and the failure to empty through closed valves when the atria do contract out of synchrony with the ventricles. Activation of pressure receptors in the atria initiate the neural reflex causing peripheral artery vasodilation and resultant decrease in mean arterial blood pressure leading to loss of consciousness. The atrial pacing forces the atria to contract at a higher rate and to empty more frequently, thereby alleviating stretching and suppressing the neural reflex. This neural reflex and the benefits of synchronized atrial pacing during unstable VT episodes are discussed in the above-referenced Hamer et al. article.

The VS-AP synchronization of the delivery of the atrial pacing pulses to a R-waves of a ventricular tachyarrhythmia that satisfies the VT detection and redetection criteria should be relatively easy to accomplish. But, while it is preferred to deliver such atrial pacing synchronized with the ventricles in the AVT (or ADD) pacing mode, it may also be possible to simply pace the atria at a higher rate than the sinus atrial rate without synchronization to the ventricular depolarizations.

One of the above described preferred embodiments contemplates the application of a CV/DEFIB shock as the anti-tachycardia therapy after a charging delay time and the delivery of the atrial pacing pulses during the charging delay time. It will be understood that the present invention can also be employed prior to and between the successive deliveries of anti-tachycardia pacing therapies that may be delivered in a sequence culminating in the delivery of one or more CV/DEFIB shock if the earlier VT therapies fail to convert the VT episode.

Moreover, under certain circumstances, it may be possible to modify the anti-tachycardia pacing therapy by delivering atrial pacing pulses synchronously with the VT terminating ventricular pacing pulses. In this way, the atrial synchronous pacing pulses may be delivered synchronously with the spontaneous ventricular depolarizations preceding and between successively delivered anti-tachycardia pacing therapies and synchronously with the delivered ventricular pacing pulses of the therapy.

While particular embodiments of the invention have been disclosed herein in detail, this has been done for the purposes of illustration only, and is not intended to limit the scope of the invention as defined in the claims which follow.

It is to be understood that various substitutions, alterations, or modifications can be made to the disclosed embodiment without departing from the spirit and scope of the claims. The above described implementations are simply those presently preferred or contemplated by the inventors, and are not to be taken as limiting the present invention to the disclosed embodiments. It is therefore to be understood, that within the scope of the appended claims, the invention may be practiced otherwise than as specifically described without actually departing from the spirit and scope of the present invention.

What is claimed is:

1. An implantable anti-tachyarrhythmia therapy delivery device comprising:
   means for sensing intrinsic depolarizations of the ventricles and providing ventricular sense signals in response;
   means for analyzing ventricular sense signals to detect occurrence of a ventricular tachyarrhythmia episode;
   an atrial pacing pulse generator operable in response to the detection of a ventricular tachyarrhythmia episode to deliver atrial pacing pulses to the atria in synchronization with sensed intrinsic depolarizations of the ventricles and at an atrial pacing rate sufficient to eject blood from the atria into the ventricles during the ventricular tachyarrhythmia to alleviate or prevent hemodynamic collapse; and anti-tachyarrhythmia therapy delivery means for generating and delivering an anti-tachyarrhythmia therapy to the ventricles of the heart following detection of the ventricular tachyarrhythmia and in a predetermined temporal relation with the delivery of the atrial pacing pulses.

2. The implantable medical device of claim 1, further comprising:

re-detection means operable following delivery of the anti-tachyarrhythmia therapy to the ventricles for analyzing the ventricular sense signals and re-detecting a ventricular tachyarrhythmia that is not terminated by the delivered anti-tachyarrhythmia therapy; and wherein:

said atrial pacing pulse generator means is operable in response to the re-detection of the ventricular tachyarrhythmia for delivering atrial pacing pulses to the atria at an atrial pacing rate sufficient to eject blood from the atria into the ventricles during the ventricular tachyarrhythmia to alleviate or prevent hemodynamic collapse pending delivery of a further anti-tachyarrhythmia therapy.

3. The implantable medical device of claim 2, wherein:

said atrial pacing pulse generator means is operable during the analysis of ventricular sense signals by said re-detection means to deliver atrial pacing pulses to the atria at an atrial pacing rate sufficient to eject blood from the atria into the ventricles during the ventricular tachyarrhythmia to alleviate or prevent hemodynamic collapse pending completion of the analysis.

4. The implantable medical device of claim 3, wherein:

said anti-tachyarrhythmia therapy delivery means comprises cardioversion/defibrillation shock delivery means for delivering a cardioversion/defibrillation shock therapy to the ventricles after a charging delay time; and said atrial pacing pulse generator means is operable during the charging delay time for delivering atrial pacing pulses to the atria at an atrial pacing rate sufficient to eject blood from the atria into the ventricles during the ventricular tachyarrhythmia to alleviate or prevent hemodynamic collapse pending delivery of the cardioversion/defibrillation shock.

5. The implantable medical device of claim 1, wherein:

said anti-tachyarrhythmia therapy delivery means comprises anti-tachycardia pacing therapy delivery means for delivering an anti-tachycardia pacing therapy.

6. The implantable medical device of claim 2, wherein:

said anti-tachyarrhythmia therapy delivery means comprises cardioversion/defibrillation shock delivery means for delivering a cardioversion/defibrillation shock therapy to the ventricles after a charging delay time; and said atrial pacing pulse generator means is operable during the charging delay time for delivering atrial pacing pulses to the atria at an atrial pacing rate sufficient to eject blood from the atria into the ventricles during the ventricular tachyarrhythmia to alleviate or prevent hemodynamic collapse pending delivery of the cardioversion/defibrillation shock.

7. The implantable medical device of claim 1, wherein:

said anti-tachyarrhythmia therapy delivery means comprises cardioversion/defibrillation shock delivery means for delivering a cardioversion/defibrillation shock therapy to the ventricles after a charging delay time; and said atrial pacing pulse generator means is operable during the charging delay time for delivering atrial pacing pulses to the atria at an atrial pacing rate sufficient to eject blood from the atria into the ventricles during the ventricular tachyarrhythmia to alleviate or prevent hemodynamic collapse pending delivery of the cardioversion/defibrillation shock.

8. The implantable medical device of claim 1, wherein the tachyarrhythmia is a ventricular tachycardia, and wherein:

said anti-tachyarrhythmia therapy delivery means comprises anti-tachycardia pacing therapy delivery means for delivering an anti-tachycardia pacing therapy; and further comprising:

re-detection means operable following delivery of the anti-tachycardia pacing therapy to the ventricles for analyzing the ventricular sense signals and re-detecting a ventricular tachycardia that is not terminated by the delivered anti-tachycardia pacing therapy; and wherein:

said atrial pacing pulse generator means is operable in response to the re-detection of the ventricular tachycardia for delivering atrial pacing pulses to the atria at an atrial pacing rate sufficient to eject blood from the atria into the ventricles during the ventricular tachycardia to alleviate or prevent hemodynamic collapse pending delivery of a further anti-tachycardia therapy.

9. The implantable medical device of claim 8, wherein:

said atrial pacing pulse generator means is operable during the analysis of ventricular sense signals by said re-detection means to deliver atrial pacing pulses to the atria at an atrial pacing rate sufficient to eject blood from the atria into the ventricles during the ventricular tachycardia to alleviate or prevent hemodynamic collapse pending completion of the analysis.

10. In an implantable medical device for detecting a ventricular tachyarrhythmia and delivering a prescribed anti-tachyarrhythmia therapy to the heart in response to a detected tachyarrhythmia, a method of preventing or alleviating hemodynamic collapse of a patient suffering cardiac insufficiency due to the ventricular tachyarrhythmia pending delivery of the anti-tachyarrhythmia therapy comprising the steps of:

sensing intrinsic depolarizations of the ventricles and providing ventricular sense signals in response;

analyzing ventricular sense signals and detecting a ventricular tachyarrhythmia;

in response to the detection of a ventricular tachyarrhythmia, delivering atrial pacing pulses to the atria in synchronization with sensed intrinsic depolarizations of the ventricles and at an atrial pacing rate sufficient to eject blood from the atria into the ventricles during the ventricular tachyarrhythmia to alleviate or prevent hemodynamic collapse; and generating and delivering an anti-tachyarrhythmia therapy to the ventricles of the heart following detection of the ventricular tachyarrhythmia and in a predetermined temporal relation with the delivery of the atrial pacing pulses.

11. The method of claim 10, further comprising the steps, following delivery of the anti-tachyarrhythmia therapy to the ventricles, of:

analyzing the ventricular sense signals to re-detect a ventricular tachyarrhythmia that is not terminated by the delivered anti-tachyarrhythmia therapy; and upon re-detection of the ventricular tachyarrhythmia, delivering atrial pacing pulses to the atria at an atrial pacing rate sufficient to eject blood from the atria into the ventricles during the ventricular tachyarrhythmia to alleviate or prevent hemodynamic collapse pending delivery of a further anti-tachyarrhythmia therapy.

12. The method of claim 10, further comprising the steps, following delivery of the anti-tachyarrhythmia therapy to the ventricles, of:

analyzing the ventricular sense signals and re-detecting a ventricular tachyarrhythmia that is not terminated by the delivered anti-tachyarrhythmia therapy; and during the analysis and upon re-detection of the ventricular tachyarrhythmia, delivering atrial pacing pulses to the atria at an atrial pacing rate sufficient to eject blood from the atria into the ventricles during the ventricular tachyarrhythmia to alleviate or prevent hemodynamic collapse pending delivery of a further anti-tachyarrhythmia therapy.

13. The method of claim 10, further comprising the steps, following delivery of the anti-tachyarrhythmia therapy to the ventricles, of:

analyzing the ventricular sense signals and re-detecting a ventricular tachyarrhythmia that is not terminated by the delivered anti-tachyarrhythmia therapy; and during the analysis, delivering atrial pacing pulses to the atria at an atrial pacing rate sufficient to eject blood from the atria into the ventricles during the ventricular tachyarrhythmia to alleviate or prevent hemodynamic collapse.

14. The implantable medical device of claim 10, wherein said anti-tachyarrhythmia therapy comprises a cardioversion/defibrillation shock therapy delivered to the ventricles after a charging delay time; and further comprising the step of:

delivering atrial pacing pulses to the atria at an atrial pacing rate sufficient to eject blood from the atria into the ventricles during the ventricular tachyarrhythmia to alleviate or prevent hemodynamic collapse pending completion of the charging delay time and delivery of the cardioversion/defibrillation shock.

15. The method of claim 14, further comprising the steps, following delivery of the anti-tachyarrhythmia therapy to the ventricles, of:

analyzing the ventricular sense signals to re-detect a ventricular tachyarrhythmia that is not terminated by the delivered anti-tachyarrhythmia therapy; and upon re-detection of the ventricular tachycardia, delivering atrial pacing pulses to the atria at an atrial pacing rate sufficient to eject blood from the atria into the ventricles during the ventricular tachyarrhythmia to alleviate or prevent hemodynamic collapse pending delivery of a further anti-tachyarrhythmia therapy.

16. The method of claim 14, further comprising the steps, following delivery of the anti-tachyarrhythmia therapy to the ventricles, of:

analyzing the ventricular sense signals and re-detecting a ventricular tachyarrhythmia that is not terminated by the delivered anti-tachyarrhythmia therapy; and during the analysis and upon re-detection of the ventricular tachyarrhythmia, delivering atrial pacing pulses to the atria at an atrial pacing rate sufficient to eject blood from the atria into the ventricles during the ventricular tachyarrhythmia to alleviate or prevent hemodynamic collapse pending delivery of a further anti-tachyarrhythmia therapy.

17. The method of claim 14, further comprising the steps, following delivery of the anti-tachyarrhythmia therapy to the ventricles, of:

analyzing the ventricular sense signals and re-detecting a ventricular tachycardia that is not terminated by the delivered anti-tachyarrhythmia therapy; and during the analysis, delivering atrial pacing pulses to the atria at an atrial pacing rate sufficient to eject blood from the atria into the ventricles during the ventricular tachycardia to alleviate or prevent hemodynamic collapse.

18. The method of claim 10, wherein:

said anti-tachyarrhythmia therapy delivery means comprises anti-tachyarrhythmia pacing therapy delivery means for delivering an anti-tachyarrhythmia pacing therapy; and further comprising the step of:

delivering atrial pacing pulses to the atria at an atrial pacing rate sufficient to eject blood from the atria into the ventricles during the ventricular tachyarrhythmia to alleviate or prevent hemodynamic collapse pending delivery of the anti-tachyarrhythmia pacing therapy.

19. The method of claim 18, further comprising the steps, following delivery of the anti-tachyarrhythmia pacing therapy to the ventricles, of:

analyzing the ventricular sense signals to re-detect a ventricular tachyarrhythmia that is not terminated by the delivered anti-tachyarrhythmia pacing therapy; and upon re-detection of the ventricular tachyarrhythmia, delivering atrial pacing pulses to the atria at an atrial pacing rate sufficient to eject blood from the atria into the ventricles during the ventricular tachyarrhythmia to alleviate or prevent hemodynamic collapse pending delivery of a further anti-tachyarrhythmia therapy.

20. The method of claim 18, further comprising the steps, following delivery of the anti-tachyarrhythmia pacing therapy to the ventricles, of:

analyzing the ventricular sense signals and re-detecting a ventricular tachyarrhythmia that is not terminated by the delivered anti-tachyarrhythmia pacing therapy; and during the analysis and upon re-detection of the ventricular tachyarrhythmia, delivering atrial pacing pulses to the atria at an atrial pacing rate sufficient to eject blood from the atria into the ventricles during the ventricular tachyarrhythmia to alleviate or prevent hemodynamic collapse pending delivery of a further anti-tachyarrhythmia therapy.

21. The method of claim 20, further comprising the steps, following delivery of the anti-tachyarrhythmia pacing therapy to the ventricles, of:

analyzing the ventricular sense signals and re-detecting a ventricular tachyarrhythmia that is not terminated by the delivered anti-tachyarrhythmia pacing therapy; and during the analysis, delivering atrial pacing pulses to the atria at an atrial pacing rate sufficient to eject blood from the atria into the ventricles during the ventricular tachyarrhythmia to alleviate or prevent hemodynamic collapse.

22. An implantable cardioverter/defibrillator adapted to be implanted in a patient's body comprising:

a cardioversion/defibrillation lead having cardioversion/defibrillation electrodes positioned for delivery of cardioversion/defibrillation shocks to the ventricles of a patient's heart;

an atrial pacing lead having at least one atrial pace/sense electrode positioned in relation to the atria of a patient's heart;

a ventricular pacing lead having at least one ventricular pace/sense electrode positioned in relation to the ventricles of a patient's heart;

a ventricular sense amplifier coupled with said ventricular pacing lead for sensing ventricular electrical depolarizations of the heart and providing ventricular sense signals in response thereto;

an atrial pacing pulse generator coupled to said atrial pacing and operative in response to atrial pace trigger signals;

cardioversion/defibrillation shock generator means for providing cardioversion/defibrillation shocks across said defibrillation lead system;

means for analyzing ventricular sense signals to detect a ventricular tachycardia;

means responsive to the detection of a ventricular tachycardia for controlling the operation of said cardioversion/defibrillation shock generator means to provide a cardioversion/defibrillation shock across said defibrillation lead system after a delay; and means for generating pace trigger signals in response to the detection of a ventricular tachycardia to cause the atrial pacing pulse generator to deliver atrial pacing pulses to the atria in synchronization with sensed intrinsic depolarizations of the ventricles and at an atrial pacing rate sufficient to eject blood from the atria into the ventricles during the ventricular tachycardia to alleviate or prevent hemodynamic collapse during said delay prior to delivery of the cardioversion/defibrillation shock.

23. The implantable cardioverter/defibriller of claim 22, wherein said atrial pace trigger generating means further comprises:

pacer timing and control means operable in a triggered pacing mode and responsive to said ventricular sense signals for providing atrial pace trigger signals to said atrial pacing pulse generator means in synchrony with said ventricular sense signals.

* * * * *